(12) United States Patent
Gers-Barlag et al.

(10) Patent No.: US 6,436,413 B1
(45) Date of Patent: *Aug. 20, 2002

(54) EMULSIFIER-FREE FINELY DISPERSE SYSTEMS OF THE WATER-IN-OIL TYPE

(75) Inventors: Heinrich Gers-Barlag, Kummerfeld; Anja Müller, Rümpel, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/385,306

(22) Filed: Aug. 30, 1999

(30) Foreign Application Priority Data

Sep. 18, 1998 (DE) .......................................... 198 42 788

(51) Int. Cl.$^7$ ................................................ A61K 7/00
(52) U.S. Cl. ...................................................... 424/401
(58) Field of Search .................................. 424/401, 59

(56) References Cited

U.S. PATENT DOCUMENTS

| 5,725,844 A | * | 3/1998 | Gers-Barlag et al. | .......... | 424/59 |
| 5,788,952 A | | 8/1998 | Gers-Barlag et al. | .......... | 424/59 |

FOREIGN PATENT DOCUMENTS

| DE | 44 25 268 A1 | 1/1996 |
| EP | 0 392 426 A2 | 10/1990 |
| EP | 0 529 396 A1 | 3/1993 |

OTHER PUBLICATIONS

Product literature for Tres BN Boron Nitrate Powders. Apr. 23, 2001.
Product literature for BN Powder Grade AC–6003. Apr. 23, 2000.

* cited by examiner

*Primary Examiner*—Jose G. Dees
*Assistant Examiner*—Konata M. George
(74) *Attorney, Agent, or Firm*—Norris McLaughlin & Marcus

(57) ABSTRACT

Pickering emulsions, which are finely disperse systems of the water-in-oil type, comprising
  (1) an oil phase,
  (2) a water phase,
  (3) at least one type of microfine particles which
    a) have an average particle size of less than 200 nm, which
    b) display both hydrophilic and lipophilic properties, i.e. which have amphiphilic character, and are dispersible both in water and in oil and which
    c) have optionally been coated on the surface,
  (4) at least one hydrocolloid and
  (5) at most 0.5% by weight of one or more emulsifiers.

6 Claims, No Drawings

EMULSIFIER-FREE FINELY DISPERSE SYSTEMS OF THE WATER-IN-OIL TYPE

The present invention relates to emulsifier-free finely disperse systems of the water-in-oil type, preferably as cosmetic or dermatological preparations.

Emulsions are generally taken to mean heterogeneous systems which consist of two liquids which are immiscible or have only limited miscibility with one another, which are usually referred to as phases. In an emulsion, one of the two liquids is dispersed in the form of very fine droplets in the other liquid.

If the two liquids are water and oil and if oil droplets are finely dispersed in water, then this is an oil-in-water emulsion (OMI emulsion, e.g. milk). The basic character of an O/W emulsion is defined by the water. In a water-in-oil emulsion (W/O emulsion, e.g. butter),. the principle is reversed, the basic character here being determined by the oil.

In order to achieve permanent dispersion of one liquid in another, emulsions in the traditional sense require the addition of an interface-active substance (emulsifier). Emulsifiers have an amphiphilic molecular structure, consisting of a polar (hydrophilic) and a nonpolar (lipophilic) molecular moiety, which are spatially separate from one another. In simple emulsions, finely disperse droplets of one phase, surrounded by an emulsifier shell, (water droplets in W/O emulsions or lipid vesicles in O/W emulsions) are present in the second phase. Emulsifiers lower the interfacial tension between the phases by positioning themselves at the interface between two liquids. At the phase boundary, they form oil/water interfacial films, which prevent irreversible coalescence of the droplets. Emulsions are frequently stabilized using emulsifier mixtures.

Traditional emulsifiers can, depending on their hydrophilic molecular moiety, be divided into ionic (anionic, cationic and amphoteric) and nonionic:

The most well-known example of an anionic emulsifier is soap, which is usually the term used for the water-soluble sodium or potassium salts of saturated or unsaturated higher fatty acids.

Important examples of cationic emulsifiers are quaternary ammonium compounds.

The hydrophilic molecular moiety of nonionic emulsifiers frequently consists of glycerol, polyglycerol, sorbitans, carbohydrates and polyoxyethylene glycols, and, in most cases, is linked to the lipophilic molecular moiety via ester and ether bonds. The lipophilic molecular moiety usually consists of fatty alcohols, fatty acids or isofatty acids.

By varying the structure and the size of the polar and nonpolar molecular moiety, the lipophilicity and hydrophilicity of emulsifiers can be varied within wide limits.

A decisive factor for the stability of an emulsion is the correct choice of emulsifiers. The characteristics of all substances present in the system are to be taken into consideration here. In the case of, for example, skincare emulsions, polar oil components and, for example, UV filters lead to instability. As well as the emulsifiers, therefore, other stabilizers are also used which, for example, increase the viscosity of the emulsion and/or act as protective colloid.

Emulsions are an important type of product in the field of cosmetic and/or dermatological preparations.

Cosmetic preparations are essentially used for skin care. The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes). If this function becomes impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important if the natural regeneration ability is inadequate. Furthermore, skincare products should protect against environmental influences, in particular against sun and wind, and delay skin ageing.

Cosmetic preparations are also used as deodorants. Such formulations are used to control body odour, which is produced when fresh perspiration, which is in itself odourless, is decomposed by microorganisms.

Medicinal topical compositions usually comprise one or more medicaments in an effective concentration. For the sake of simplicity, in order to distinguish clearly between cosmetic and medicinal use and corresponding products, reference is made to the legal provisions in the Federal Republic of Germany (e.g. Cosmetics Directive, Foods and Drugs Act).

The use of customary emulsifiers in cosmetic or dermatological preparations is in itself acceptable. Nevertheless, emulsifiers, like ultimately any chemical substance, may in certain circumstances cause allergic reactions or reactions based on oversensitivity of the user.

For example, it is known that certain light dermatoses are triggered by certain emulsifiers, but also by various fats and simultaneous exposure to sunlight. Such light dermatoses are also called "Mallorca acne". There has thus been no lack of attempts to reduce the amount of customary emulsifiers to a minimum, in the ideal case even to zero.

A reduction in the required amount of emulsifier can, for example, be achieved by taking advantage of the fact that very finely divided solid particles have an additional stabilizing action. The solid substance accumulates at the oil/water phase boundary in the form of a layer, as a result of which coalescence of the disperse phases is prevented. It is not the chemical properties of the solid particles which are of fundamental importance here, but the surface properties.

Around 1910, Pickering prepared paraffin/water emulsions which were stabilized merely by the addition of various solids, such as basic copper sulphate, basic iron sulphate or other metal sulphates. This type of emulsion is thus also referred to as a Pickering emulsion.

The original forms of Pickering emulsions initially surfaced, as it were, as undesired secondary effects in a variety of industrial processes, such as, for example, in secondary oil recovery, the extraction of bitumen from tar sand and other separation processes involving two immiscible liquids and fine, dispersed solid particles. These are generally W/O emulsions which are stabilized by mineral solids. Accordingly, investigation of corresponding systems, such as, for example, the oil/water/soot or oil/water/slate dust systems was initially the focus of research activity.

Basic experiments have shown that one characteristic of a Pickering emulsion is that the solid particles are arranged at the interface between the two liquid phases, where they form, as it were, a mechanical barrier against the combining of the liquid droplets.

It is a relatively new technical development to use Pickering emulsions as a base for cosmetic or dermatological preparations.

One way of achieving solids stabilization in the sense of a pickering emulsion in a cosmetic or dermatological preparation is, according to May-Alert (*Pharmazie in unserer Zeit* [*Pharmacy in our time*], Vol. 15, 1986, No. 1, 1–7) for example, to use emulsifier mixtures which comprise both anionic and cationic surfactants. Since mixing anionic and cationic surfactants always results in the precipitation of insoluble, electroneutral compounds, deliberate precipitation of these neutral surfactants in the oil/water interface makes it possible to achieve additional solids stabilization.

European Laid-open Specification 0 686 391, moreover, describes "emulsions" of the water-in-oil type which are free from surface-active substances and are stabilized only by solids. Stabilization is achieved here using spherical polyalkylsilsesquioxane particles which have a diameter of from 100 nm up to 20 μm, which are added to the oil phase and thicken it. This type of preparation can therefore also be referred to as oil gels (also: oleogels), into which water can be stably dispersed.

Pickering emulsions are stabilized by the use of suitable solids or pigments. However, the preparations of the prior art generally have the disadvantage that they are limited to a narrow field of application or a restricted choice of raw materials since they can only be stably formulated in this manner. For many areas of cosmetics (e.g. for the field of face care), Pickering emulsions of the prior art have unsatisfactory cosmetic properties.

The object was therefore to remedy the disadvantages of the prior art. In particular, the intention was to provide cosmetic and dermatological bases for cosmetic and dermatological preparations which are characterized by good skin tolerability.

In addition, an object of the present invention was to provide products with the widest possible variety of applications. For example, the intention was to provide bases for preparation forms such as cleansing emulsions, facecare and bodycare preparations or deodorants, but also distinctly medicinal-pharmaceutical presentations, for example preparations against acne and other skin conditions.

It was surprising and in no way predictable by the person skilled in the art that Pickering emulsions, which are finely disperse systems of the water-in-oil type, comprising
(1) an oil phase,
(2) a water phase,
(3) at least one type of microfine particles which
   a) have an average particle size of less than 200 nm, which
   b) display both hydrophilic and lipophilic properties, i.e. which have amphiphilic character, and are dispersible both in water and in oil and which
   c) have optionally been coated on the surface,
(4) at least one hydrocolloid and
(5) at most 0.5% by weight of one or more emulsifiers, overcome the disadvantages of the prior art.

According to the invention, it is particularly advantageous if the preparations comprise significantly less than 0.5% by weight of one or more emulsifiers. Very particular preference is given to preparations according to the invention which are entirely free from emulsifiers in the traditional sense.

The preparations according to the invention are extremely satisfactory preparations in every respect which have considerably higher stability compared with traditional Pickering emulsions and are therefore suitable in particular to serve as bases for preparation forms having diverse application purposes. W/O Pickering emulsions within the meaning of the present invention are, surprisingly, markedly stable.

In addition, the preparations according to the invention are characterized by excellent skin tolerability. In addition, it was surprising that preparations according to the invention, which are in the form of a sunscreen, exhibit higher effectiveness than customary sunscreen formulations.

While preparations of the prior art having a pigment content of as little as 1% by weight produce a dull feel following their application to the skin, which increases further with higher pigment concentrations, the preparations according to the invention, surprisingly, do not leave a dry or dull impression on the skin, but on the contrary exhibit excellent cosmetic properties.

Although the prior art recognizes, in addition to Pickering emulsions, emulsifier-free, finely disperse cosmetic or dermatological preparations, which are generally referred to as hydrodispersions and which are dispersions of a liquid, semisolid or solid inner (discontinuous) lipid phase in an outer aqueous (continuous) phase, these preparations are oil-in-water formulations.

The prior art was therefore unable to point the way to the present invention.

W/O Pickering emulsions for the purposes of the present invention are available by dispersing amphiphilic particles suitable for the preparation of W/O Pickering emulsions and which are in accordance with the invention into the fatty phase.

"Hydrocolloid" is the technical abbreviation for the more correct term "hydrophilic colloid". Hydrocolloids are macromolecules which have a largely linear structure and have intermolecular forces of interaction, which permit secondary and primary valence bonds between the individual molecules and thus the formation of a reticular-structure. Some are water-soluble natural or synthetic polymers which, in aqueous systems, form gels or viscous solutions. They increase the viscosity of the water by either binding water molecules (hydration) or else by absorbing and encapsulating the water into their interwoven macromolecules, at the same time restricting the mobility of the water.

The group of hydrocolloids can be divided as follows into:
  organic, natural compounds, such as, for example, agar agar, carrageen, tragacanth, gum arabic, alginates, pectins, polyoses, guar gum, carob bean flour, starch, dextrins, gelatins, casein,
  organic, modified natural substances, such as, for example, carboxymethylcellulose and other cellulose ethers, hydroxyethyl and -propylcellulose and the like,
  organic, completely synthetic compounds, such as, for example, polyacrylic and polymethacrylic compounds, vinyl polymers, polycarboxylic acids, polyethers, polyimines, polyamides, inorganic compounds, such as, for example, polysilicic acids, clay minerals such as montmorillonites, zeolites, silicas.

Examples of hydrocolloids which are preferred according to the invention are methylcelluloses, which -is the name for the methyl ethers of cellulose. They are characterized by the following structural formula Structral formula I

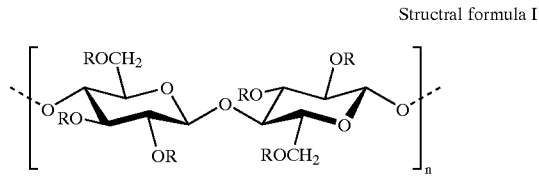

in which R may be a hydrogen or a methyl group.

Particularly advantageous for the purposes of the present invention are the cellulose mixed ethers, which are generally likewise referred to as methylcelluloses, which contain, in addition to a dominating content of methyl groups, also 2-hydroxyethyl, 2-hydroxypropyl or 2-hydroxybutyl groups. Particular preference is given to (hydroxypropyl) methylcelluloses, for example those available under the trade name Methocel E4M from Dow Chemical Comp.

Also advantageous according to the invention is sodium carboxymethylcellulose, the sodium salt of the glycolic ether of cellulose, for which R in structural formula I can be a hydrogen and/or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, which is an anionic heteropolysaccharide, which is generally formed by fermentation from maize sugar and is isolated as potassium salt. It is produced from Xanthomonas campestris and some other species under aerobic conditions with a molecular weight of from $2\times10^6$ to $24\times10^6$. Xanthan is formed from a chain having β-1,4-bonded glucose (cellulose) with side chains. The structure of the subgroups ("repeat units") consists of glucose, mannose, glucuronic acid, acetate and pyruvate.

Other hydrocolloids which are advantageous according to the invention are polymers of acrylic acid, in particular those which are chosen from the group of carbomers or Carbopols (Carbopol® is actually a registered trade mark of the B. F. Goodrich Company). Carbopols are compounds of the general structural formula

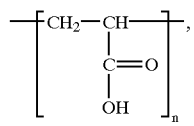

whose molecular weight can be between about 400,000 and more than 4,000,000. The group of Carbopols also includes acrylate-alkyl acrylate copolymers, for example those characterized by the following structure:

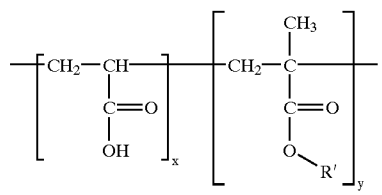

where R' is a long-chain alkyl radical and x and y are numbers which symbolize the respective stoichiometric content of each comonomer. These Carbopols, too, are also advantageous for the purposes of the present invention.

Examples of advantageous Carbopols are the grades 907, 910, 934, 940, 941, 951, 954, 980, 981, 1342, 1382, 2984 and 5984, it being possible for these compounds to be present individually or in any combination with one another. Particular preference is given to Carbopol 981, 1382 and 5984 (either individually or in combination with other hydrocolloids).

Also advantageous for the purposes of the present invention are the copolymers, comparable with the acrylate-alkyl acrylate copolymers, of $C_{10-30}$-alkyl acrylates and one or more monomers of acrylic acid, of methacrylic acid or esters thereof. The INCI name for such compounds is "Acrylates/C 10–30 Alkyl Acrylate Crosspolymer". Particularly advantageous are those available under the trade names Pemulen TR1 and Pemulen TR2 from B. F. Goodrich Company.

The total amount of one or more hydrocolloids in the finished cosmetic or dermatological W/O-Pickering emulsions is advantageously chosen to be less than 1.0% by weight, preferably between 0.01 and 0.5% by weight, based on the total weight of the preparations.

It is also advantageous, although not obligatory, for the Pickering emulsions according to the invention to comprise other auxiliaries which can additionally increase the stability of these preparations, for example substances which are chosen from the group of waxes and/or oil thickeners, and of electrolytes.

It is also advantageous for the Pickering emulsions according to the invention to comprise auxiliaries which can contribute to reducing or preventing a dull or dry feel on the skin following their application, where it is possible that the main purpose of these substances is a different one. Preferably, these substances are, for example, chosen from the group of unsymmetrically substituted s-triazine derivatives, cyclodextrins, film formers and polymeric moisturizers, it being possible for these substances to be present either individually or in a mixture.

The cosmetic properties of the Pickering emulsions according to the invention can additionally, for example, be further improved by also using oils in the oil phase which have a viscosity of less than 30 mPa.s, in particular of less than 20 mPa.s (determined using a rheometer from Contraves (Rheomat 108E) at a shear gradient of 500/s and a temperature of 25° C.).

Microfine Particles

The amphiphilic character of the microfine particles according to the invention is evident, for example, from the fact that they are dispersible both in water and in oil.

It is advantageous to choose the average particle diameter of the particles used to be between 1 nm and 200 nm, particularly advantageously between 5 nm and 100 nm.

It is also advantageous to choose the concentration of all amphiphilic particles according to the invention to be greater than 0.1% by weight, particularly advantageously between 0. 1% by weight and 30% by weight, based on the total weight of the preparations.

For the purposes of the present invention, advantageous particles are all those which are suitable for stabilizing Pickering W/O emulsions. It is essentially insignificant for the present invention in which of the potentially naturally occurring modifications the particles are present.

To stabilize the Pickering emulsions, preference is given to using untreated, virtually pure pigment particles, in particular those which can be used as dyes in the food industry and/or as absorbers of UV radiation in sunscreens. Examples of advantageous pigments are the zinc oxide pigments available from Merck which are available under the trade names Zinkoxid neutral from Haarmann & Reimer or NanoX from Harcros Chemical Group.

For the purposes of the present invention, Pickering emulsions are likewise advantageously stabilized by inorganic pigments which have been surface-treated ("coated") to repel water, where at the same time the intention is to form or retain the amphiphilic character. This surface-treatment can consist in providing the pigments with a thin hydrophobic layer by processes known per se.

One such process, which is described below using titanium dioxide as an example, consists in, for example, producing the hydrophobic surface layer according to the following reaction

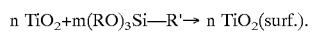

n and m are arbitrary stoichiometric parameters, and R and R' are the desired organic radicals. Particularly advantageous are $TiO_2$ pigments, for example those coated with aluminium stearate, available under the trade name MT 100 T from TAYCA.

A further advantageous coating of the inorganic pigments consists of dimethylpolysiloxane (also: dimethicone), a mixture of completely methylated, linear siloxane polymers which are terminally blocked with trimethylsiloxy units. For the purposes of the present invention, particularly advantageous pigments are zinc oxide pigments which are coated in this way.

Also advantageous is a coating of the inorganic pigments with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments have been additionally coated with aluminium hydroxide or hydrated aluminium oxide (also alumina, CAS No.: 1333-84-2). Particularly advantageous are titanium dioxides which have been coated with simethicone and alumina, it being possible for the coating to also comprise water. One example thereof is the titanium dioxide available under the trade name Eusolex T2000 from Merck.

For the purposes of the present invention it is also advantageous to use a mixture of different pigment types either within a crystal, for example as mixed iron oxide, or by combination of two or more pigment types within a preparation.

The Pickering emulsions are also preferably stabilized by boron nitride particles, for example by the boron nitrides listed below:

| Trade name | Available from |
| --- | --- |
| Boron Nitride Powder | Advanced Ceramics |
| Boron Nitride Powder | Sintec Keramik |
| Ceram Blanche | Kawasaki |
| HCST Boron Nitride | Stark |
| Tres BN ® | Carborundum |
| Wacker-Bornitrid BNP | Wacker-Chemie |

It is advantageous to choose the average particle diameter of the boron nitride particles used to be less than 20 µm, particularly advantageously less than 15 µm. For the purposes of the present invention, Pickering emulsions are likewise advantageously stabilized by boron nitride particles which have been surface-treated ("coated") to repel water, where at the same time the intention is to form or retain the amphiphilic character.

An advantageous coating of the boron nitride particles consists of dimethylpolysiloxane (dimethicone). The boron nitride particles treated with dimethicone and available from Carborundum under the trade name Tres BN® UHP 1106 are advantageous, for example.

Also advantageous is a coating of the boron nitride particles with polymethylhydrogensiloxane, a linear polysiloxane which is also referred to as methicone. Advantageous boron nitride particles treated with methicone are, for example, those available from Carborundum under the trade name Tres BN® UHP 1107.

It is also advantageous to stabilize the Pickering emulsions according to the invention using microfine polymer particles.

For the purposes of the present invention, examples of advantageous microfine polymer particles are polycarbonates, polyethers, polyethylenes, polypropylenes, polyvinyl chloride, polystyrene, polyamides, polyacrylates and the like.

Advantageous according to the invention are, for example, microfine polyamide particles which are available under the trade name SP-500 from TORAY. Also advantageous are polyamide 6 (also: nylon 6) and polyamide 12 (also: nylon 12) particles. Polyamide 6 is the polyamide formed from ε-aminocaproic acid (6-aminohexanoic acid) or ε-caprolactam [poly(ε-caprolactam)], and polyamide 12 is a poly(c-laurolactam) from ε-Iaurolactam. For the purposes of the present invention, Orgasol® 1002 (polyamide 6) and Orgasol® 2002 (polyamide 12) from ELF ATOCHEM, for example, are advantageous.

Other advantageous polymer particles are microfine polymethacrylates. Such particles are available, for example, under the trade name POLYTRAP® from DOW CHEMICAL.

It is particularly advantageous, but not obligatory, if the microfine polymer particles used have been surface-coated. This surface-treatment can consist in providing the pigments with a thin hydrophilic layer by processes known per se.

Advantageous coatings consist, for example, of $TiO_2$, $ZrO_2$ or also other polymers, such as, for example, polymethyl methacrylate.

Particularly advantageous microfine polymer particles for the purposes of the present invention are also obtainable by the process, described in U.S. Pat. Specification No. 4,898,913, for the hydrophilic coating of hydrophobic polymer particles.

It is advantageous to choose the average particle diameter of the microfine polymer particles used to be less than 100 μm, particularly advantageously less than 50 μm. In this connection, it is essentially insignificant in which form (platelets, rods, spherules, etc.) the polymer particles used are present.

In addition, it is advantageous to stabilize the Pickering emulsions according to the invention using modified polysaccharides.

For the purposes of the present invention, modified polysaccharides are, for example, obtainable by reaction of starch with mono-, bi- or polyfunctional reagents or oxidizing agents in reactions which proceed in a largely polymer-analogous manner.

Such reactions are based essentially on modifications of the hydroxyl groups of the polyglucans by etherification, esterification or selective oxidation. This produces, for example, so-called starch ethers and starch esters of the general structural formula Structural formula (II)

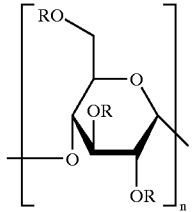

in which R can, for example, be a hydrogen and/or an alkyl and/or an aralkyl radical (in the case of starch ethers) or a hydrogen and/or an organic and/or inorganic acid radical (in the case of starch esters). Starch ethers and starch esters are advantageous, modified polysaccharides for the purposes of the present invention.

Particularly advantageous starch ethers are, for example, those which are obtainable by etherification of starch with tetramethylolacetylenediurea and which are referred to as non-mucilaginous starch (nonswelling starch).

Also particularly advantageous are starch esters and salts thereof, for example the sodium and/or aluminium salts of half-esters of starch which have low degrees of substitution, in particular sodium starch n-octenyl succinate of the structural formula (II) in which R is characterized by the following structure

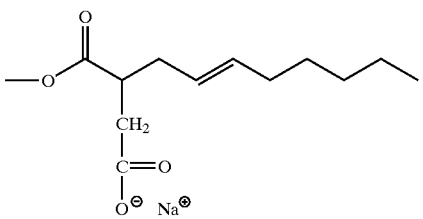

and which is available, for example, under the trade name Amiogum® 23 from CERESTAR, and aluminium starch octenyl succinates, in particular those available under the trade names Dry Flo® Elite LL and Dry Flo® PC from CERESTAR.

It is advantageous to choose the average particle diameter of the modified polysaccharide used to be less than 20 μm, particularly advantageously less than 15 μm.

The list of given modified polysaccharides which are able to stabilize Pickering emulsions according to the invention is of course not intended to be limiting. For the purposes of the present invention, modified polysaccharides are obtainable in a large number of ways known per se, both of a chemical and a physical nature.

Also particularly advantageous for stabilizing W/O Pickering emulsions are magnesium silicates (also: talc), for example those available under the trade name Talkum Micron from Grolmann.

The water phase proportion in the W/O Pickering emulsions according to the invention is preferably chosen from the range of from 0.5 to 75% by weight, based on the total weight of the formulations.

It is also advantageous, but not obligatory, to combine the microfine particles according to the invention with other amphiphilic particles which may or may not also be able to contribute to the stabilization of the Pickering emulsions.

Such particles are, for example, titanium dioxide pigments which have been coated with octylsilanol, and/or silicon dioxide particles which have been surface-treated to repel water. Suitable silicon dioxide particles are, for example, spherical polyalkylsilsesquioxane particles, as mentioned in European Laid-open Specification 0 686 391. Such polyalkylsilsesquioxane particles are available, for example, under the trade names Aerosil R972 and Aerosil 200V from Degussa. Suitable titanium dioxide particles are available under the trade name T805, also from Degussa.

Oil Phase

The oil phase of the O/W emulsions according to the invention is advantageously chosen from the group of polar oils, for example from the group of lecithins and fatty acid triglycerides, namely the triglycerol esters of saturated and/or unsaturated, branched and/or unbranched alkane carboxylic acids having a chain length of from 8 to 24, in particular from 12 to 18, carbon atoms. The fatty acid triglycerides can be advantageously chosen, for example, from the group of synthetic, semisynthetic and natural oils, such as, for example, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

For the purposes of the present invention, other advantageous polar oil components can also be chosen from the group of esters of saturated and/or unsaturated, branched and/or unbranched alkane carboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, such as, for example, jojoba oil.

In addition, the oil phase can advantageously be chosen from the group of dialkyl ethers, the group of saturated or unsaturated, branched or unbranched alcohols. It is particularly advantageous for the oil phase of the O/W emulsions according to the invention to have a content of $C_{12-15}$-alkyl benzoate or to consist entirely of this.

Any desired mixtures of such oil and wax components can also be used advantageously for the purposes of the present invention. In some instances, it can also be advantageous to use waxes, for example cetyl palmitate, as the sole lipid component of the oil phase.

In addition, the oil phase of the O/W emulsions according to the invention can likewise advantageously, but not obligatorily, also comprise nonpolar oils, for example those which are chosen from the group of branched and unbranched hydrocarbons and hydrocarbon waxes, in particular vaseline (petrolatum), paraffin oil, squalane and squalene, polyolefins and hydrogenated polyisobutenes. Of the polyolefins, polydecenes are the preferred substances.

The oil phase can advantageously also have a content of cyclic or linear silicone oils or consist entirely of such oils, although it is preferred to use an additional content of other oil phase components apart from the silicone oil or the silicone oils.

Advantageously, cyclomethicone (octamethylcyclotetrasiloxane) is used as silicone oil to be used according to the invention. However, other silicone oils are also to be used advantageously for the purposes of the present invention, for example hexamethylcyclotrisiloxane, polydimethylsiloxane, poly(methylphenylsiloxane).

The Pickering emulsions according to the invention can be used as bases for cosmetic or dermatological formulations. These can have the customary composition and be used, for example, for the treatment and care of the skin, as lipcare products, as deodorant products and as make-up products or make-up remover products in decorative cosmetics or as light protection preparations. For use, the cosmetic and dermatological preparations according to the invention are applied to the skin in sufficient amounts in the manner customary for cosmetics.

Accordingly, for the purposes of the present invention, cosmetic or topical dermatological compositions may, depending on their structure, be used, for example, as skin-protection creams, cleansing milks, sunscreen lotions, nourishing creams, day creams or night creams, etc. In some instances, it is possible and advantageous to use the compositions according to the invention as bases for pharmaceutical formulations.

The cosmetic and dermatological preparations according to the invention can comprise cosmetic auxiliaries, as are customarily used in such preparations, e.g. preservatives, bactericides, perfumes, antifoams, dyes, pigments which have a colouring effect, further thickeners, emollients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

In particular, the Pickering emulsions according to the invention may also comprise antioxidants. According to the invention, favourable antioxidants which can be used are any antioxidants suitable or conventional for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-camosine, D-carnosine, L-camosine and derivatives thereof (e.g. anserine), carotenoids, carotenes (e.g. α-carotene, carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and the salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, c-glycosylrutin, ferulic acid, furfurylideneglucitol, carnosine, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and its derivatives (e.g. selenomethionine), stilbenes and their derivatives (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably from 0.001 to 30% by weight, particularly preferably from 0.05 to 20% by weight, in particular 0.1 to 10% by weight, based on the total weight of the preparation.

If vitamin E and/or derivatives thereof are used as the antioxidant or antioxidants, their arespective concentrations are advantageously chosen from the range of 0.001 to 10% by weight, based on the total weight of the formulation.

If vitamin A or vitamin A derivatives or carotenes or derivatives thereof are used as the antioxidant or antioxidants, their respective concentrations are advantageously chosen from the range of 0.001–10% by weight, based on the total weight of the formulation.

Cosmetic and dermatological preparations which are in the form of a sunscreen are also favourable. These preferably comprise at least one UV-A filter substance and/or at least one UV-B filter substance and/or at least one further inorganic pigment selected from the group consisting of the oxides of iron, zirconium, silicon, manganese, aluminium, cerium and mixtures thereof and also modifications in which the oxides are the active agents.

For the purposes of the present invention, it is, however, also advantageous to provide such cosmetic and dermatological preparations whose main purpose is not protection against sunlight, but which nevertheless comprise substances which protect against UV. For example, UV-A and UV-B filter substances are commonly incorporated into day creams.

UV protection substances, like antioxidants and, if desired, preservatives, also represent effective protection of the preparations themselves against decay.

The preparations according to the invention can advantageously comprise substances which absorb UV radiation in the UV-A and/or UV-B range, the total amount of filter substances being, for example, from 0.1% by weight to 30% by weight, preferably from 0.5 to 20% by weight, in particular from 1.0 to 15.0% by weight, based on the total weight of the preparations, in order to provide cosmetic preparations which protect the hair and/or the skin from the whole of ultraviolet radiation. They can also be used as sunscreens for hair and skin.

Advantageous UV-A filter substances for the purposes of the present invention are dibenzoylmethane derivative, in particular 4-(tert-butyl)-4'-methoxydibenzoylmethane (CAS No. 70356-09-1), which is sold by Givaudan under the name Parsol® 1789 and by Merck under the trade name Eusolex® 9020.

Other advantageous UV-A filter substances are phenylene-1,4-bis(2-benzimidazyl)-3,3'-5,5'-tetrasulphonic acid:

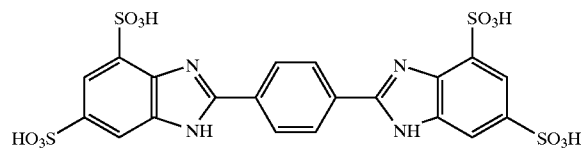

and its salts, particularly the corresponding sodium, potassium or triethanolammonium salts, in particular the bis-sodium salt of phenylene-1,4-bis(2-benzimidazyl)-3,3'-5,5'-tetrasulphonic acid:

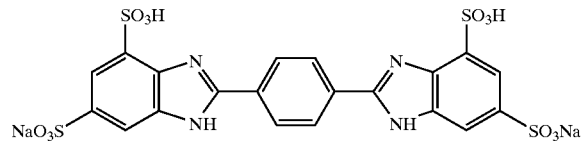

and 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulphonic acid) and is characterized by the following structure:

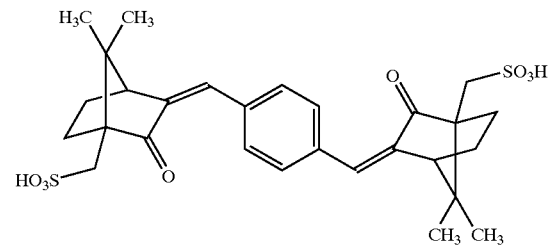

For the purposes of-the present invention, advantageous UV filter substances are also so-called broadband filters, i.e. filter substances which absorb both UV-A and UV-B radiation.

Advantageous broadband filters and/or UV-B filter substances are, for example, bisresorcinyltriazine derivatives having the following structure:

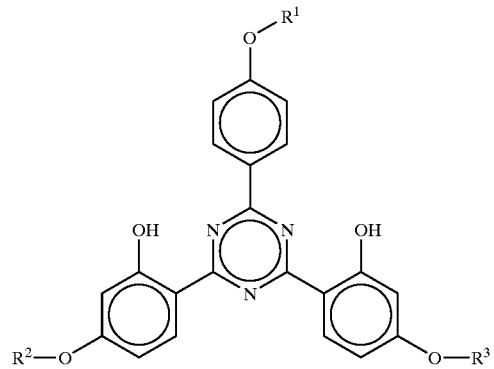

where $R^1$, $R^2$ and $R^3$ independently of one another are chosen from the group of branched and unbranched alkyl groups having from 1 to 10 carbon atoms, or a single hydrogen atom. Particular preference is given to 2,4-bis-{[4-(2-ethylhexyloxy)-2-hydroxy]phenyl}-6-(4- methoxyphenyl)-1,3,5-triazine and tris(2-ethylhexyl) 4,4', 4"-(1,3,5-triazine-2,4,6-triyltriimino)trisbenzoate, synonym: 2,4,6-tris[anilino(p-carbo-2'-ethyl-1'-hexyloxy)]-1,3,5-triazine, which is marketed by BASF Aktiengesellschaft under the trade name UVINUL® T 150.

Other UV filter substances, which have the structural formula

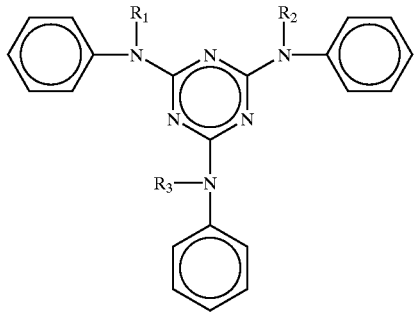

are also advantageous UV filter substances for the purposes of the present invention, for example the s-triazine derivatives described in European Laid-open Specification EP 570 838 A1, the chemical structure for which is given by the generic formula

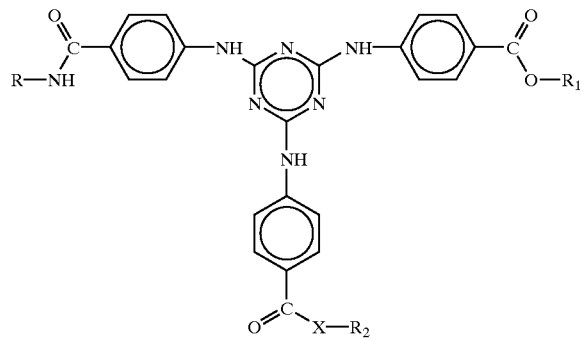

where
R is a branched or unbranched $C_1-C_{18}$-alkyl radical, a $C_5-C_{12}$-cycloalkyl radical, optionally substituted with one or more $C_1-C_4$-alkyl groups,
X is an oxygen atom or an NH group,
$R_1$ is a branched or unbranched $C_1-C_{18}$-alkyl radical, a $C_5-C_{12}$-cycloalkyl radical, optionally substituted with one or more $C_1-C_4$-alkyl groups, or a hydrogen atom, an alkali metal atom, an ammonium group or a group of the formula

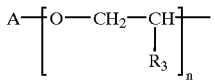

in which
A is a branched or unbranched $C_1-C_{18}$-alkyl radical, a $C_5-C_{12}$-cycloalkyl or aryl radical, optionally substituted with one or more $C_1-C_4$-alkyl groups,
$R_3$ is a hydrogen atom or a methyl group,
n is a number from 1 to 10,
$R_2$ is a branched or unbranched $C_1-C_{18}$-alkyl radical, a $C_5-C_{12}$-cycloalkyl radical, op2ionally substituted by one or more $C_1-C_4$-alkyl groups, when X is the NH group, and
is a branched or unbranched $C_1-C_{18}$-alkyl radical, a $C_5-C_{12}$-cycloalkyl radical, optionally substituted with one or more $C_1-C_4$-alkyl groups, or a hydrogen atom, an alkali metal atom, an ammonium group or a group of the formula

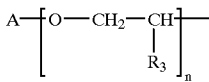

in which
A is a branched or unbranched $C_1-C_{18}$-alkyl radical, a $C_5-C_{12}$-cycloalkyl or aryl radical, optionally substituted with one or more $C_1-C_4$-alkyl groups,
$R_3$ is a hydrogen atom or a methyl group,
n is a number from 1 to 10,
when X is an oxygen atom.

An example of such unsymmetrically substituted s-triazines is dioctylbutylamidotriazone.

Other UV filter substances, whose incorporation into cosmetic or dermatological light protection formulations hitherto had problems, are also known. For example, European Laid-open Specification 775 698 describes bisresorcinoltriazine derivatives, the chemical structure for which is given by the generic formula

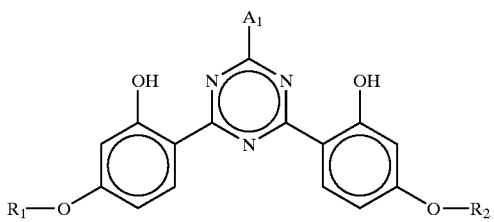

where $R_1$, $R_2$ and $A_1$ represent very different organic radicals.

Also advantageous for the purposes of the present invention are 2,4-bis{[4-(2-ethylhexyloxy)-2-hydroxy]phenyl}-6-(4-methoxyphenyl)-1,3,5-triazine, 2,4-bis{[4-(3-sulfonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triaine, 2,4-bis{[4-tris(trimethylsiloxysilyipropyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5', 5', 5'-heptamethylsiloxy-2"-methylpropyloxy)-2-hydroxy]phenyl}-6-(4-methoxyphenyl)-1,3,5-triazine.

Another advantageous UV filter for the purposes of the present invention is 2,2'-methylenebis(6-(2H-benzotriazol-2-yl)-4-(1,1,3,3-tetramethylbutyl)phenol), which is characterized by the chemical structural formula

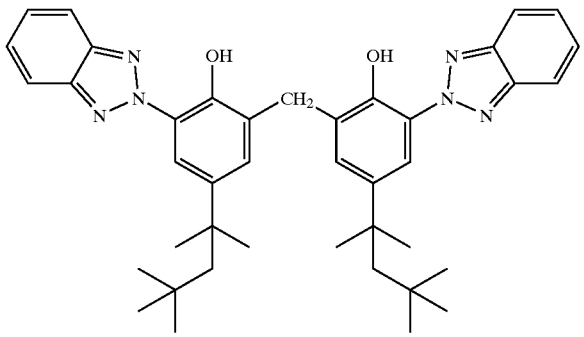

Also advantageous for the purposes of the present invention is 2-(2H-benzotriazol-2-yl)-4-methyl-6-[2-methyl-3-[1,3,3,3-tetramethyl-1-[(trimethylsilyl)oxy]disiloxanyl]propyl]phenol (CAS-No.: 155633-54-8) having the INCI name Drometrizole Trisiloxane, which is characterized by the chemical structural formula

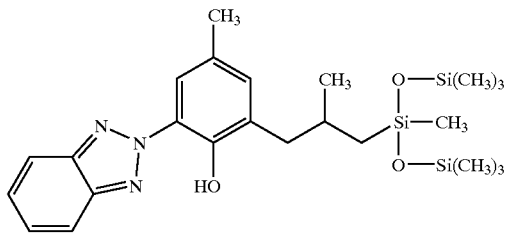

The UV-B filters can be oil-soluble or water-soluble. Examples of advantageous oil-soluble UV-B filter substances are:

- 3-benzylidenecamphor derivates, preferably 3-(4-methylbenzylidene)camphor, 3-benzylidenecamphor;
- 4-aminobenzoic acid derivates, preferably 2-ethylhexyl 4-(dimethylamino)benzoate, amyl 4-(dimethylamino)benzoate;
- 2,4,6-trianilino-(p-carbo-2'-ethyl-1'-hexyloxy)-1,3,5-triazine;
- Esters of benzalmalonic acid, preferably di(2-ethylhexyl) 4-methoxybenzalmalonate;
- Esters of cinnamic acid, preferably 2-ethylhexyl 4-methoxycinnamate, isopentyl 4-methoxycinnamate;
- Derivates of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Examples of advantageous water-soluble UV-B filter substances are:

- Salts of 2-phenylbenzimidazol-5-sulphonic acid, such as its sodium, potassium or triethanolammonium salts, and the sulphonic acid itself;
- Sulphonic acid derivates of 3-benzylidenecamphor, such as, for example, 4-(2-oxo-3-bornylidenmethyl)benzenesulphonic acid, 2-methyl-5-(2-oxo-3-bornylidenemethyl)sulphonic acid and salts thereof.

Another light protection filter substance to be used advantageously according to the invention is 2-ethylhexyl 2-cyano-3,3-diphenylacrylate (octocrylene), which is available from BASF under the name Uvinul® N 539 and is characterized by the following structure:

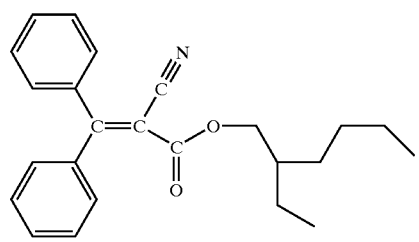

It can also be of considerable advantage to use polymer-bonded or polymer UV filter substances in preparations according to the present invention, in particular those described in WO-A-92/20690.

In addition, it may in some circumstances be advantageous to incorporate other UV-A and/or UV-B filters according to the invention into cosmetic or dermatological preparations, for example certain salicylic acid derivatives such as 4-isopropylbenzyl salicylate, 2-ethylhexyl salicylate (=octyl salicylate), homomenthyl salicylate.

The list of given UV filters which can be used for the purposes of the present invention is of course not intended to be limiting.

Preparations according to the invention can also be advantageously used as bases for cosmetic deodorants and antiperspirants, so that a particular embodiment of the present invention relates to Pickering emulsions as bases for cosmetic deodorants.

Cosmetic deodorants are used to control body odour which arises when fresh perspiration, which is in itself odourless, is decomposed by microorganisms. Customary cosmetic deodorants are based on various modes of action.

In antiperspirants, astringents, mainly aluminium salts, such as aluminium hydroxychloride (aluminium chlorohydrate), reduce the formation of perspiration.

The use of antimicrobial substances in cosmetic deodorants can reduce the bacterial flora of the skin. In an ideal situation, only the microorganisms which cause the odour should be effectively reduced. The flow of perspiration itself is not influenced as a result, and in ideal circumstances, only microbial decomposition of perspiration is stopped temporarily.

The combination of astringents and antimicrobial active substances in one and the same composition is also common.

All active ingredients common for deodorants or antiperspirants can advantageously be used, for example odour concealers, such as customary perfume constituents, odour absorbers, for example the phyllosilicates described in Laid-open Patent Specification DE 40 09 347, of these in particular montmorillonite, kaolinite, illite, beidellite, nontronite, saponite, hectorite, bentonite, smectite, and also, for example, zinc salts of ricinoleic acid. Antibacterial agents are also suitable to be incorporated into the novel W/O emulsion sticks. Advantageous substances are, for example, 2,4,4'-trichloro-2'-hydroxy diphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol) and also the active ingredients or active ingredient combinations described in the Laid-open Patent Specifications DE-A-37 40 186, DE-A-39 38 140, DE-A-42 04 321, DE-A-42 29 707, DE-A-43 09 372, DE-A-44 11 664, DE-A-195 41 967, DE-A-195 43 695, DE-A-195 43 696, DE-A-195 47 160, DE-A-196 02 108, DE-A-196 02 110, DE-A-196 02 111, DE-A-196 31 003, DE-A-196 31 004 and DE-A-196 34 019, and the Patent Specifications DE-42 29 737, DE-42 37 081, DE43 24 219, DE-44 29 467, DE-44 23 410 and DE-195 16 705. Sodium hydrogencarbonate can also be used advantageously.

The list of specified active ingredients and active ingredient combinations is of course not intended to be limiting.

The amount of antiperspirant active ingredients or deodorants (one or more compounds) in the preparations is preferably from 0.01 to 30% by weight, particularly preferably from 0.1 to 20% by weight, in particular 1–10% by weight, based on the total weight of the preparation.

The examples below serve to illustrate the present invention without limiting it. The numerical values in the examples are percentages by weight, based on the total weight of the respective preparations.

EXAMPLES

|  | 1 W/O | 2 W/O | 3 W/O |
|---|---|---|---|
| Titanium dioxide (Eusolex T2000) | 2 | 4 | 6 |
| Zinc oxide | 5 |  | 4 |
| Titanium dioxide (Titandioxid T805) |  |  | 2 |
| Silica (Aerosil R972) |  | 1 | 0.5 |
| Talc (Talkum Micron) |  | 0.5 |  |
| Boron nitride |  | 2 |  |
| Hydroxystearyl hydroxystearate (Elfacos C26) | 2 |  | 2 |
| $C_{20-40}$-alkyl stearate (Kesterwachs K82) | 1 | 1 |  |
| $C_{16-38}$-alkylhydroxystearolyl stearate (Kesterwachs k80P) |  | 2 |  |
| Behenoxy dimethicone (Abil Wax 2440) |  |  | 5 |
| Polyisobutene (Rewopal PIB 1000) | 5 |  |  |
| Caprylic/capric triglyceride | 5 | 5 | 5 |
| Octyldodecanol | 5 |  | 5 |
| Mineral oil | 10 |  |  |
| Butylene glycol caprylate/caprate |  | 10 | 10 |
| $C_{12-15}$-alkyl benzoate | 10 | 10 | 10 |
| Dimethicone |  | 2 | 3 |
| Hydrogenated polyisobutene (Polysynlan) | 2 |  |  |
| Methylbenzylidenecamphor |  | 3 |  |
| Octyltriazone |  | 1 |  |
| Dibenzoylmethane |  | 2 |  |
| Dioctylbutamidotriazone (UVASORB HEB) |  | 2 |  |
| Preservative | 0.5 | 0.5 | 0.5 |

-continued

|  | 1 W/O | 2 W/O | 3 W/O |
|---|---|---|---|
| Glycerol | 5 | 10 | 3 |
| Biosaccharide gel (Fucogel 1000) |  |  | 5 |
| NaCl | 1 |  | 1 |
| MgSO$_4$ |  | 0.5 |  |
| Phenylbenzimidazolesulphonic acid |  | 1 |  |
| Carbomer (Carbopol 981) |  | 0.1 |  |
| $C_{10-30}$-alkyl acrylate crosspolymer (Pemulen TR1) |  |  | 0.01 |
| Xanthan gum | 0.05 |  |  |
| Sodium carboxylmethylcellulose (Natrosol Plus 330 CS) |  | 0.05 | 0.01 |
| NaOH 45% strength solution in water |  | 0.3 | 0.01 |
| EDTA solution |  | 1 |  |
| Water | ad 100 | ad 100 | ad 100 |

What is claimed is:

1. Pickering emulsions, which are finely disperse water-in-oil systems, comprising (1) an oil phase, (2) a water phase, (3) microfine particles which a) have an average particle size of less than 200 nm, which b) display both hydrophilic and lipophilic properties, and are dispersible both in water and in oil and which c) have optionally been coated on the surface, (4) at least one hydrocolloid and (5) at most 0.5% by weight of one or more emulsifiers.

2. Pickering emulsions according to claim 1, wherein said emulsions are emulsifier-free.

3. Pickering emulsions according to claim 1, wherein the content of the particles used is between 0.1% by weight and 30% by weight, based on the total weight of the preparations.

4. Pickering emulsions according to claim 1, wherein the particle diameter of the particles used is between 5 nm and 100 nm.

5. Pickering emulsions according to claim 1, wherein the microfine particles used are selected from the group cinsisting of amphiphilic metal oxides, microfine polymer particles, modified polysaccharides and mixtures thereof.

6. Pickering emulsions according to claim 1, wherein the particles used have been surface-treated to repel water and the amphiphilic character of the particles is formed or retained.

* * * * *